(12) United States Patent
Sodder et al.

(10) Patent No.: US 7,529,243 B2
(45) Date of Patent: May 5, 2009

(54) APPARATUS AND METHOD FOR A VIRTUAL HIERARCHICAL LOCAL AREA NETWORK

(75) Inventors: Arnold Sodder, Newton, MA (US); Timothy Mancour, Wrentham, MA (US); Louis Didiodato, Toronto (CA)

(73) Assignee: Enterasys Networks, Inc., Andover, MA (US)

( * ) Notice: Subject to any disclaimer, the term of this patent is extended or adjusted under 35 U.S.C. 154(b) by 583 days.

(21) Appl. No.: 10/621,849

(22) Filed: Jul. 16, 2003

(65) Prior Publication Data

US 2004/0081203 A1    Apr. 29, 2004

Related U.S. Application Data

(60) Provisional application No. 60/396,884, filed on Jul. 16, 2002.

(51) Int. Cl.
*H04L 12/56* (2006.01)
*H04L 12/66* (2006.01)

(52) U.S. Cl. ................. 370/392; 370/401; 370/469; 370/471

(58) Field of Classification Search ................. None
See application file for complete search history.

(56) References Cited

U.S. PATENT DOCUMENTS

| | | | |
|---|---|---|---|
| 5,490,252 A | 2/1996 | Macera et al. | |
| 5,655,140 A | 8/1997 | Haddock | |
| 5,796,944 A | 8/1998 | Hill et al. | |
| 6,167,513 A | 12/2000 | Inoue et al. | |
| 6,331,978 B1 * | 12/2001 | Ravikanth et al. | 370/392 |
| 7,161,946 B1 * | 1/2007 | Jha | 370/401 |
| 2002/0024964 A1 | 2/2002 | Baum et al. | |
| 2002/0037010 A1 | 3/2002 | Yamauchi | |
| 2002/0138628 A1 * | 9/2002 | Tingley et al. | 709/227 |
| 2003/0026271 A1 * | 2/2003 | Erb et al. | 370/401 |
| 2003/0118053 A1 * | 6/2003 | Edsall et al. | 370/474 |
| 2004/0003110 A1 * | 1/2004 | Ozguner | 709/236 |
| 2006/0239298 A1 * | 10/2006 | Townsley et al. | 370/470 |

FOREIGN PATENT DOCUMENTS

JP    2002-344476    11/2002

OTHER PUBLICATIONS

Liu, Huey-Ing et al, "Virtual private dial-up services over multi-protocol label switching networks," *Computer Communications*, vol. 25:884-889 (2000).
Japanese Office Action for Application No. 2004-521946, dated Nov. 28, 2008.

* cited by examiner

*Primary Examiner*—Chi H. Pham
*Assistant Examiner*—Soon D. Hyun
(74) *Attorney, Agent, or Firm*—Lahive & Cockfield, LLP

(57) ABSTRACT

A method and apparatus are provided for creating a virtual hierarchical local area network. The method and apparatus provide a hierarchical framing technique that allows a network architecture to realize a local area network hierarchy within the network. In this manner, a first local area network hierarchy is defined by communication in a first frame format between a first set of network devices and a second set of network devices. A second local area network hierarchy is defined by communication in a second frame format between members of the second set of network devices. The second frame format includes the fields of a frame in the first frame format that is used to communicate between the first set of communication devices and the second set of communication devices.

25 Claims, 11 Drawing Sheets

US 7,529,243 B2

APPARATUS AND METHOD FOR A VIRTUAL HIERARCHICAL LOCAL AREA NETWORK

RELATED APPLICATIONS

The current application claims priority to Provisional Patent Application Serial No. 60/396,884, entitled METHODS AND APPARATUS FOR PROVIDING DATA SERVICES USING VIRTUAL HIERARCHICAL BRIDGING, filed on Jul. 16, 2002.

TECHNICAL FIELD OF THE INVENTION

The present invention generally relates to network communications and, more particularly, to an apparatus and method for communication of data in a network.

BACKGROUND OF THE INVENTION

Conventional network architectures are often difficult to scale to meet an increase or decrease in the number network users due in part to the number of data link layer addresses that the various network devices must maintain. Moreover, network architectures that are difficult to scale are often not cost effective to operate due to the burden to scale to meet changes in the number of network users. Cost effective methods and devices provide a reduction in deployment and operating costs for the network provider or operator, which, in turn, can provide a cost savings to a user of the network. Moreover, network providers and operators seek devices that can readily adapt to increased network and user demands (i.e. scalability). For example, network providers and operators often desire a device that can preserve plug-and-play characteristics of bridges while scaling a network size to connect one LAN to another LAN, or to connect one WAN to another WAN, or to connect a LAN or WAN to a network core.

Consequently, a need exists for a device that readily handles an increase or decrease in network size without limiting network service to router connections. Moreover, use of a device that preserves plug-and-play characteristics of bridges provides a cost effective option to the network provider or operator while readily adapting to network size and offering a simplified network control plane that reduces replication and learning overhead in the network.

SUMMARY OF THE INVENTION

The illustrative embodiment of the present invention provides a method and device that enables the deployment of a network architecture having a hierarchy achieved through tiered data link layer addressing. The methods and devices of some embodiments of the present invention allow communications in a data link layer protocol between a first set of communication devices in network and a second set of communication devices to identify a first network hierarchy. The method and device of the present invention allow communications in a data link layer protocol between the second set of communication devices and a third set of communication devices to identify a second network hierarchy. The illustrative embodiment of the present invention also allows communications in a data link layer protocol between members of the third set of communication devices in the network to identify a third hierarchy in the network.

The illustrative embodiment of the present invention provides an approach that allows a communication device in a network to receive a frame, to add a second data link layer header to the received frame and forward the frame with the second data link layer header to another communication device in the network for delivery to a destination node. The illustrative embodiment of the present invention supports connectionless access to the network and supports a connection oriented network core. The illustrative embodiment of the present invention allows communications devices in the network to reduce the size of MAC address tables maintained by each device and allows communication devices associated with the network core to reduce signaling and replication overhead. Furthermore, the method and device of the illustrative embodiment of the present invention reduces the number of tunnel labeled switch paths required if the network core is configured to operate in accordance with a multi-protocol label switching (MPLS) standard.

One aspect of the present invention includes an apparatus associated with a network. The apparatus includes an input to receive a frame in a first format from a first node of the network and a framing mechanism to add another data link layer header to the frame in the first format to form a frame in a second frame format. The apparatus further includes an output to transmit or forward the frame in the second frame format to a second node of the network. The apparatus includes a processor to control operation of the apparatus. Furthermore, the framing mechanism of the apparatus is configurable to add a trailer to the frame in the first format when formatting the frame to the second frame format. The apparatus is configurable to perform functions characteristic of a bridge and functions characteristic of a switch.

The frame in the first format includes a first field to hold an address specifying an address associated with a device in the network that is sending the frame in the first frame format. The frame in the first frame format also includes a second field to hold an address specifying an address associated with a device in the network to receive the frame in the first frame format.

In another aspect of the present invention, a method is performed in an electronic device associated with a network. The steps of the method include taking action to receive a frame in a first frame format on an input of the electronic device and formatting the frame in the first frame format into a second frame format. The first frame format includes a header identifying a first hierarchy of the network. The second frame format includes a header identifying a second hierarchy of the network. The step of formatting can include a step of appending a trailer to the frame in the first frame format. The step of formatting is further capable of encapsulating the frame in the first frame format to format the frame into the second frame format. The method can further include the step of forwarding the frame in the second frame format based on a destination address from the first frame format.

The first frame format includes fields for a first MAC source address and a first MAC destination address. The second frame format includes fields for a second MAC source address and a second MAC destination address.

In another aspect of the present invention a method is performed in a network of electronic devices. Performance of the method forwards data from a first end node electronic device to a second end node electronic device. The method is performed by formatting the data into a first format. The first format includes a first field to hold a data link layer address specifying the first end node electronic device and a second field to hold a data link layer address specifying the second end node electronic device. The data in the first format is forwarded from the first end node electronic device to a first intermediate node electronic device. At the first intermediate node electronic device, the data in the first format is encapsulated with a plurality of fields to format the data into a second format. The second format includes a first field to hold a data link layer address specifying the first intermediate node electronic device and a second field to hold a data link layer address specifying a second intermediate node electronic device. Once the data is in the second format, the data is forwarded in the second format from the first intermediate node electronic device to the second intermediate node electronic device for forwarding of the data in the first format to the second end node electronic device.

The first format of the data includes an Ethernet format. In addition, the second frame format further includes a field to hold a transmission error detection value. The transmission error detection value includes a checksum value or a cyclic redundancy check (CRC) value.

In a further aspect of the present invention, a device readable medium holding device readable instructions for performing a method in an electronic device associated with a network is disclosed. The method includes the step of parsing a portion of a frame in a first frame format received on an input of the electronic device to identify a destination address of the frame. The first frame format has a first data link layer source address and a first data link layer destination address. The method also performs the step of formatting the frame in the first frame format into a second frame format in the electronic device. The second frame format has a second data link layer source address and a second data link layer destination address. The step of formatting can include a step of inserting the frame in the first frame format into a field of the frame in the second frame format. The step of formatting can further include the step of encapsulating the frame in the first frame format with a header having a field to hold a second data link layer source address, a field to hold a second data link layer destination address and a trailer having a field to hold a transmission detection error value. The method can further include the performance of the step of forwarding the frame in the second format based on the first data link layer destination address from the first frame format.

BRIEF DESCRIPTION OF THE DRAWINGS

The illustrative embodiment of the present invention will be described below relative to the following drawings.

DETAILED DESCRIPTION

The illustrative embodiment of the present invention facilitates frame processing in a network environment to allow the network to increase or decrease the number of nodes in the network while preserving the beneficial ability to configure the network using network devices having the characteristics of bridges. The method and apparatus of the illustrative embodiment allow a network to realize a virtual hierarchical local area network service (VHLS) by allowing network communications with frames using a tiered data link layer address. That is, the method and apparatus of the illustrative embodiment of the present invention allow communications over a first portion of the network with frames having a first data link layer header and format those frames into a second format by adding a second data link layer header for communications over a second portion of the network.

The method and apparatus of the present invention format the frames from the first portion of the network into the second format and also formats frames from the second portion of the network back to the first format for communication over the first portion of the network. In this manner, the frame in the first format identifies a first network hierarchy and the frames in the second format identify a second network hierarchy. The modification of a frame having a data link layer header to include a second data link layer header allows a network to realize a LAN hierarchy, which, in turn, simplifies core network operations by reducing MAC address table sizes of core edge devices and core devices. The modification of a frame having a data link layer header to include a second data link layer header further allows a core network configured to support MPLS to reduce the number of tunnels or pseudo wires in the core.

Before continuing with the discussion below it is helpful to first define a few terms used herein.

The term "host device" as used herein, refers to an electronic device associated with a user of a network and is capable of formatting data into a data link layer compatible frame.

The term "network device" as used herein, refers to an electronic device or apparatus configured for use in a network environment that is able to understand and perform operations with data according to a data link layer protocol. A network device includes at least one port for communicating with a "host device" and at least one port for communicating with another "network device", or a "core edge device".

The term "core edge device" as used herein, refers to an electronic device that provides access to a network's core or backbone.

Figure 1:
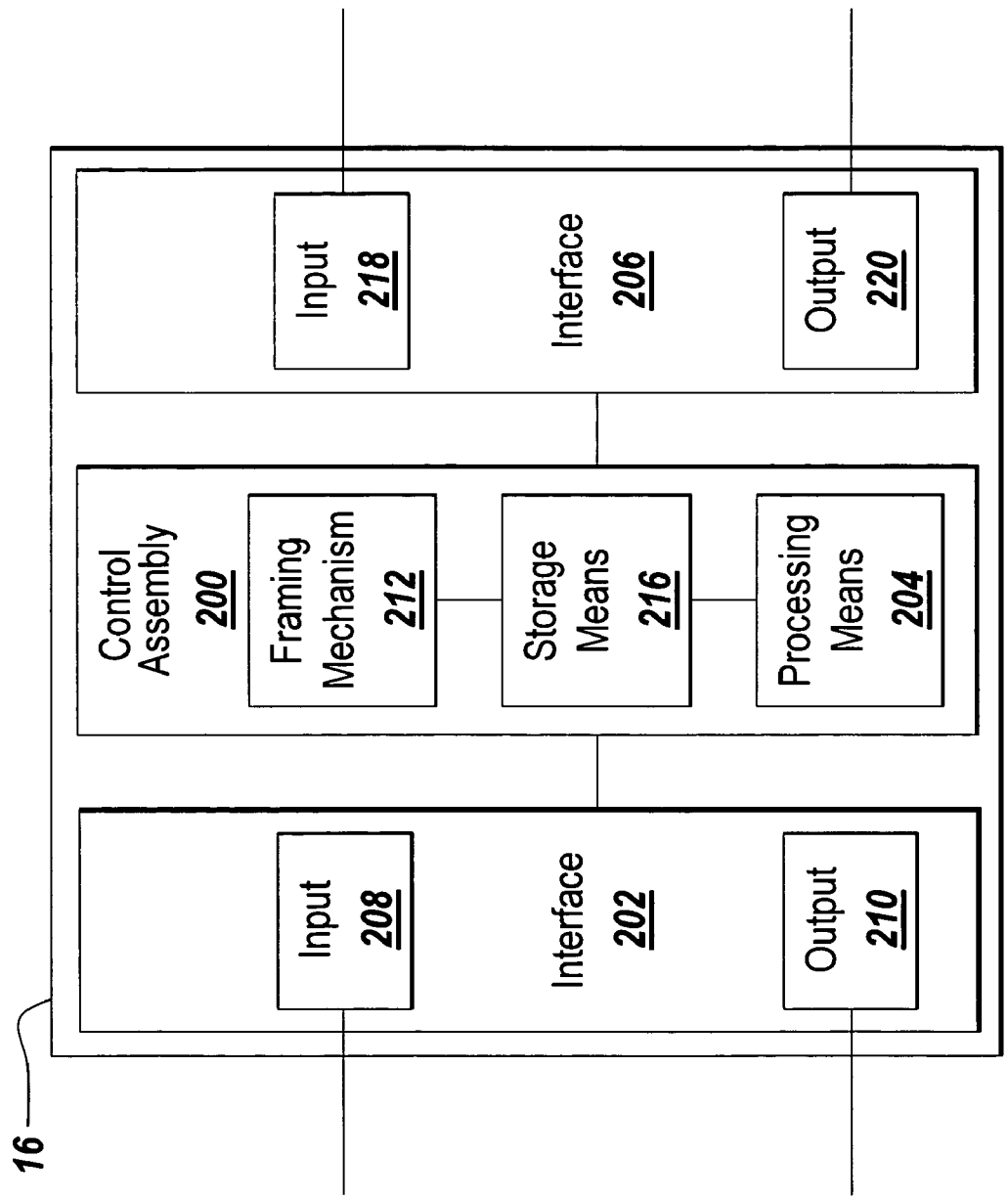
FIG. 1 illustrates an exemplary apparatus suitable for use in practicing the illustrative embodiment of the present invention.

FIG. 1 illustrates an apparatus suitable for practicing the illustrative embodiment of the present invention. Network device 16 represents network device suitable for performing layer two data communications, such as a bridge or a switch. The network device 16 includes an interface 202, control assembly 200, and an interface 206. The control assembly 200 interfaces with the interface 202 and interface 206 to control processing of received frames and control transmission or forwarding of processed frames. The control assembly 200 controls the processing of the received frames from a first format to a second format and from a second format to a first format. Furthermore, the control assembly 200 operates to provide control of the network device 16 by monitoring and controlling various operations of the network device 16, interfacing with other network equipment and systems such as, network management systems, either directly or indirectly through an intermediary such as an interface of an element management system associated with the network device 16.

The interface 202 includes an input 208 to receive frames and an output 210 to forward or transmit frames. The interface 206 includes an input 218 to receive frames and an output 220 to forward or transmit frames. The network device 16 is configurable to have the interface 202 face one or more host devices associated with a user of the network and to have the interface 206 face one or more network devices, or core edge devices associated with the operator or provider of the network. When configured in this manner, the interface 202 receives frames in a frame format 24 or frame format 36 on the input 208 and forwards or transmits frames in the frame format 24 or the frame format 36 on the output 210. The frame format 24 and the frame format 36 are discussed below in more detail with respect to FIG. 2. In like fashion, the interface 206 receives frames in a frame format 48 on the input 218 and forwards or transmits frames in the frame format 48 on the output 220. The frame format 48 is discussed below in more detail with respect to FIG. 2.

The framing mechanism 212 formats the frames received on the input 208 into a suitable frame format for transmission on the output 220. for example, the frame format 48. In like fashion, the framing mechanism 212 formats the frames received on the input 218 into a suitable frame format for transmission on the output 210, for example, the frame format 24 or the frame format 36. The framing mechanism is configurable to include a number of hardware modules, software modules, or both to format frames from a first format to a second format and visa versa. Those skilled in the art will also recognize that interface 202 and interface 206 are configurable as one or more software components, one or more hardware components, or a combination of one or more software components and one or more hardware components.

The framing mechanism 212 reads and writes to the storage means 216 to format the frames in the appropriate format. The storage means 216 includes a look up table, or other suitable means such as a database and database manager to hold various MAC addresses, virtual private network (VPN) identifiers, and other like information of a network in which the network device 16 operates. The framing mechanism 212 writes to the storage means 216 when it learns of a new MAC address, a new VPN identifier, or other like information. The framing mechanism 212 reads from the storage means 216 to determine a forwarding or destination MAC address when formatting a frame from a first format to a second format.

Figure 2:
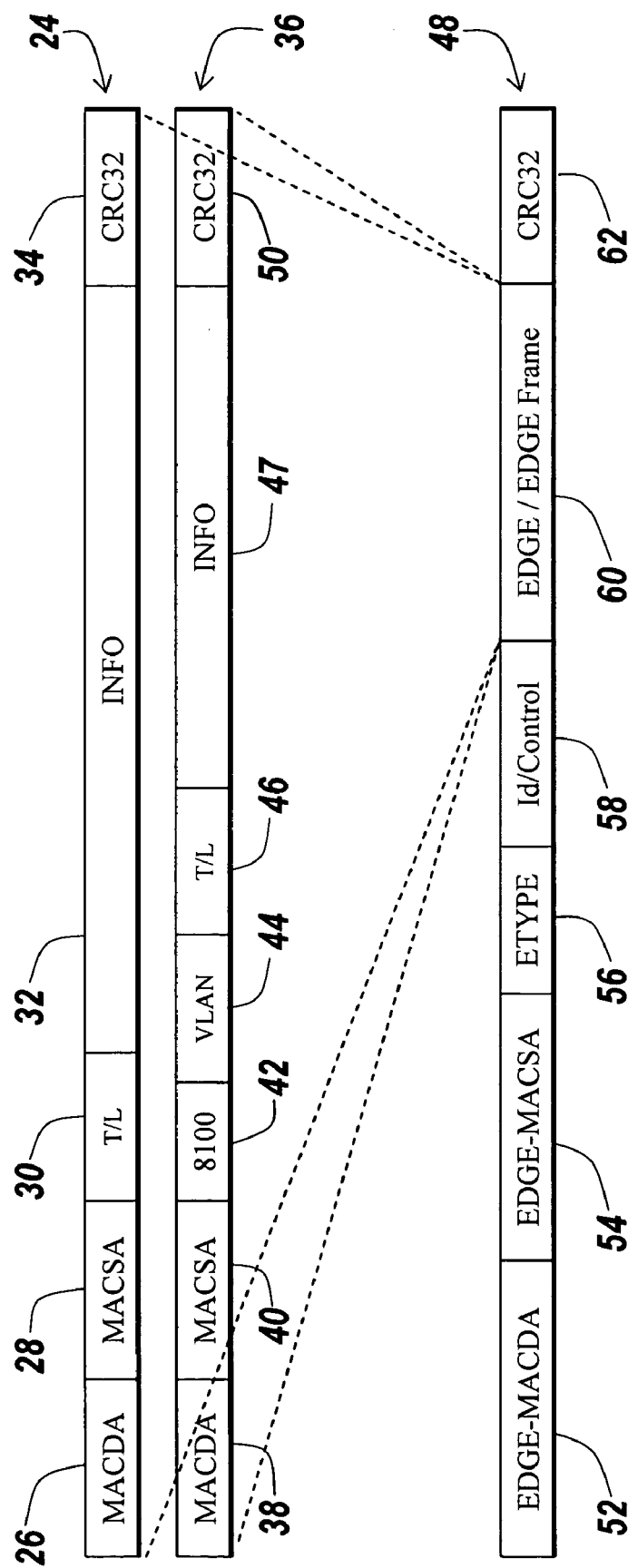
FIG. 2 illustrates frame formats suitable for use in practicing the illustrative embodiment of the present invention.

FIG. 2 illustrates frame formats suitable for use in practicing the illustrative embodiment of the present invention. Frame format 24 includes a destination address field 26 to hold a MAC address specifying a destination device in a network, a source address field 28 to hold a MAC address specifying the source device of the frame, a type length field 30 to hold a value specifying the type of frame and the length of data held in the frame, and data field 32 to hold data. The frame format 24 includes a frame check sequence field 34 to hold a value for indicating a transmission error such as a CRC value, a checksum value, or other like value. Frame format 24 is compatible with the various Ethernet frame formats, for example, an Ethernet II frame. Nevertheless, those skilled in the art will recognize that other Ethernet frame formats are suitable for practicing the present invention, for example, frame formats compatible with Ethernet 802.2, Ethernet SNAP, and Ethernet 802.3.

Frame format 36 is similar to frame format 24, but includes two additional fields to hold information relating to virtual local area networks (VLAN) or VLAN tags. Frame format 36 includes a destination field 38 to hold a MAC address specifying a destination device for the frame, a source address field 40 to hold a MAC address specifying the source device of the frame, a type/length field 46 to hold data to identify the type of Ethernet frame and the length of the data held in field 47, and field 50 to a hold a value for use in detection of transmission errors. Additionally, frame format 36 includes field 42 to hold information that identifies a VLAN protocol identifier, and field 44 to hold information identifying the priority of the frame and identifying the VLAN to which the frame belongs.

Frame format 48 illustrates a hierarchical encapsulated MAC frame that encapsulates a frame in frame format 24 or a frame in frame format 36. Frame format 48 includes an optional field 58, which is discussed below in more detail. The formatting of a frame from frame format 24 or frame format 36 to frame format 48 is carried out by the framing mechanism 212. Details of the operations carried out by the network device 16 to format a received frame into frame format 48 are discussed below in more detail.

Frame format 48 includes a field 52 to hold a MAC address specifying a destination device, a field 54 to hold a MAC address specifying a source device of the frame in frame format 48, a field 56 to hold information specifying the Ethernet type, field 58 to hold information specifying a virtual private network (VPN) identifier and control word, for example a layer two virtual private network (L2VPN) identifier, a field 60 to hold a frame in frame format 24 or frame format 36, and a field to hold a value for indicating transmission errors of a frame in frame format 48.

A frame having the frame format 48 includes the entire frame in frame format 24 or frame format 36. In this manner the original transmission error detection value of the frame is preserved, allowing detection errors of the information held in field 60 due to transmission in the frame format 48. Use of a frame in frame format 48 also allows a network device to modify the information held in field 60 and calculate and add a new error detection value to the frame held in field 60, alternatively a network device may strip the transmission error detection value off of the frame held in field 60.

Frame format 48 illustrates a hierarchical MAC-in-MAC address scheme or a tiered MAC address scheme. This hierarchical approach allows many host device MAC addresses to be represented by a single MAC address or by a combination of a single MAC address and a VPN identifier. Moreover, if the network architecture includes a core portion configured for MPLS, operation of the core is simplified by reducing the number of label switch paths (LSP), tunnels, or pseudo wires required to traverse the core.

Figure 3:
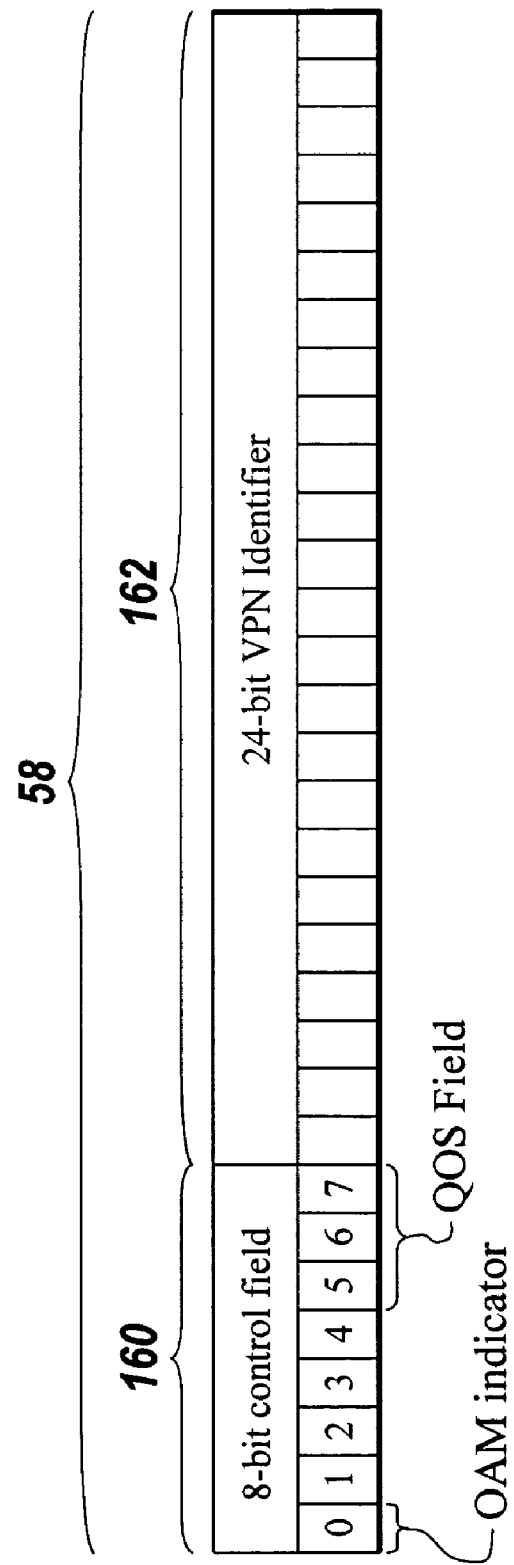
FIG. 3 illustrates a field from the frame format illustrated in FIG. 2 in more detail.

FIG. 3 illustrates field 58 in more detail. Field 58 includes an 8 bit control field 160 and a 24 bit VPN identifier 162. Field 160 represents a virtual hierarchical local area network control field. Field 162 holds a VPN identifier for a network configured to provide virtual hierarchical local area network services by using MAC-in-MAC style frames such as frames in frame format 48. The 24 bit VPN identifier is used to separate data between network users and is globally unique for a provider's network. Bit 0 of the 8 bit control field 160 is an operation, administration and maintenance (OAM) indicator. Bit 1 in control field 160 is used to indicate if the information in field 60 includes a transmission error detection value. Bits 2-4 are typically unassigned and bits 5-7 define a quality of service (QOS) field.

Those skilled in the art will recognize that the use of the QOS field is dependent on the architecture of the provider's network. For example, use of the QOS field can provide multi-tiered QOS as part of a network providers services. Multi-tiered QOS is useful to provide preferential treatment of control frames such OAM and Spanning Tree Bridge bridge protocol data units (BPDU's) at each intermediary node of the network as well as within the core of the network. In some cases, the network provider or operator can provide a different path to carry certain packets, for example, broadcast data. In this manner, a network device practicing the illustrative embodiment of the present invention can signal a pseudo wire to carry broadcasts of all virtual private networks as compared to for example network devices configured to provide virtual private local area network switching (VPLS) where such a network device must signal a separate pseudo wire to carry broadcast data for each VPN.

Figure 4A:
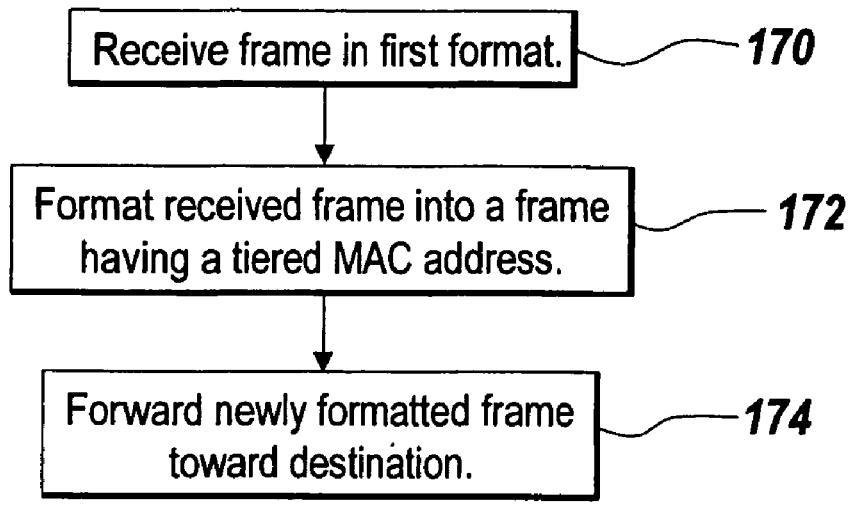
FIG. 4A illustrates steps taken to practice the illustrative embodiment of the present invention.

FIG. 4 illustrates a block flow diagram suitable for practicing the illustrative embodiment of the present invention. FIG. 4 is discussed in relation to the network device 16 illustrated in FIG. 1. In step 170, the network device 16 receives a frame on input 208 in a first format, for example frame format 24 or frame format 36 or any other suitable Ethernet format. The first frame format includes a data link layer header and trailer along with a data field. The interface 202 passes the frame in the first format from the input 208 to the control assembly 200 for processing. In step 172, the frame in the first format is processed in the control assembly 200 by the framing mechanism 212 and the processing means 204.

The processing means 204 is able to control the flow a frames into the control assembly 200 allowing the framing mechanism 212 to parse the frame in the first format to determine the destination of the frame and perform an address look up in the storage means 216 to determine the MAC address of a network device associated with the host destination device. If the framing mechanism 212 finds a MAC address of the network device associated with the host destination device, the framing mechanism 212 adds another data link layer header to the frame in the first format to form a tiered MAC address frame or a MAC-in-MAC frame. Framing mechanism 212 can also add a trailer to the frame in the first format to encapsulate the frame in the first frame format to format the frame into a frame in the second frame format such as, frame format 48. As part of formatting the frame from the first frame format to the second frame format the framing mechanism 212 writes the MAC address of the network device found in the storage means 216 into field 52 and writes the MAC address of the network device 16 in field 54. The framing mechanism 212 can also perform a CRC or a checksum of the frame in the second frame format and place the resulting value in field 62. In this manner, all of the values in the received frame are preserved, for example in field 60 of the second frame format 48. When the newly formatted frame is ready for further transmission in the network to the host destination device, the control assembly 200 passes the newly formatted frame to the interface 206 for transmission or forwarding on output 220.

In step 174, the newly formatted frame is forwarded to the network device specified in field 52, which, in turn upon receipt of the frame in frame format 48, strips off or decapsulates all of the fields except for field 60 and forwards the contents of field 60 to the destination host device identified by a destination address in field 26 or field 38 depending of the first frame format. Those skilled in the art will recognize that the network device to which network device 16 forwards the frame in format 48 is also configured as the network device 16.

Figure 4B:
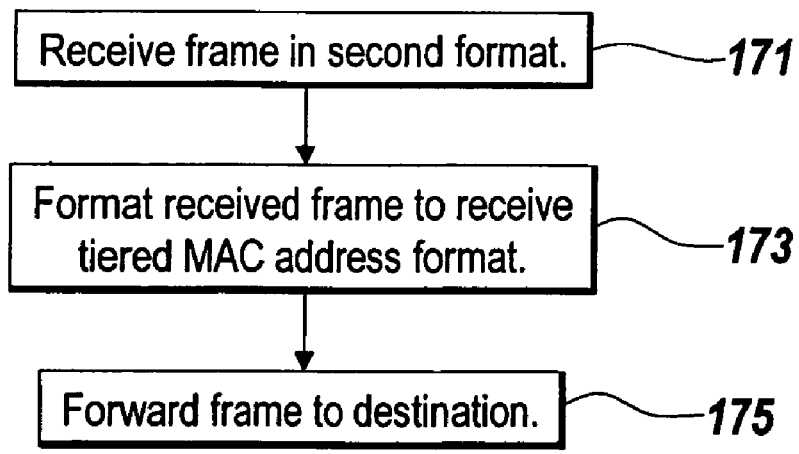
FIG. 4B illustrates steps taken to practice the illustrative embodiment of the present invention.

FIG. 4B illustrates the steps taken by the network device 16 to process a frame received in the second frame format 48. In step 171, network device 16 receives a frame in frame format 48 on input 208 or input 218. In step 173, the framing mechanism 212 operates to strip off fields 52, 54, 56, 58, and 62 to leave the frame held in frame in field 60. In step 175, the network device 16 forwards the frame held in field 60, that is, a frame in frame format 24 or frame format 36 to the address specified in field 26 or field 38.

Those skilled in the art will appreciate that the processing means 204 controls the operation of the control assembly 200 and controls the operation of the network device 16 either directly or indirectly through other hardware and software modules and components. For example, the processing means 204 can control the number of frames received, processed and transmitted by network device 16 to assist in controlling traffic flow through a network. The processing means 204 can also perform self diagnostics on the features of network device 16 and provide a status of its health assessment to another network device. Moreover, the processing means 204 can perform or oversee other various functions such as aging MAC addresses held by the storage means and deleting or discarding those that have not been used after a selected number of events, such as days, frames handled or other suitable metrics. Furthermore, those skilled in the art will recognize that network device 16 is able to learn the MAC address of a network device through the use of a broadcast frame or other suitable method for learning other network devices in communication with network device 16.

Figure 5:
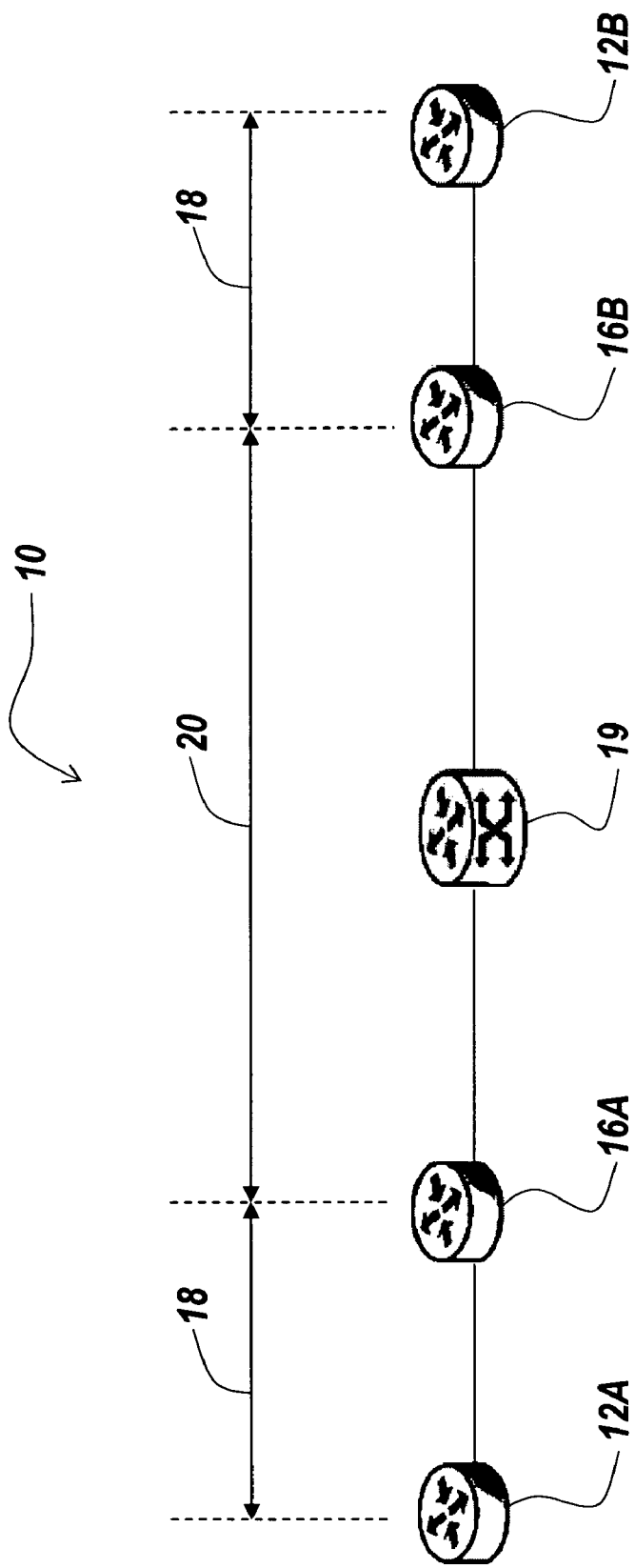
FIG. 5 illustrates an exemplary network environment suitable for practicing the illustrative embodiment of the present invention.

FIGS. 5 through 10 depict the illustrative embodiment of the present invention from the perspective of a network environment. FIG. 5 illustrates an exemplary network environment suitable for practicing the illustrative embodiment of the present invention. The network 10 includes host device 12A and host device 12B. Those skilled in the art will recognize that use of the terms "source" and the term "destination" herein are merely meant to facilitate explanation of the illustrative embodiment of the present invention and are not meant to imply unidirectional traffic through or across the network 10. The network 10 also includes network device 16A, network device 16B and network device 19. Network devices 16A and 16B represent network device 16 discussed above. Network device 19 represents a core edge device providing access to the backbone of the network. Moreover, those skilled in the art will recognize that network 10 can include a significant number of host devices and network devices without departing from the intended scope of the present invention.

Host device 12A communicates with network device 16A in a connectionless manner preferably using Ethernet frames. Communications between the host device 12A and the network device 16A identify a first network domain 18. Likewise communications between host device 12B and the network device 16B can occur in a connectionless manner preferably using Ethernet frames and also identify a first network domain 18. The first network domain 18 is a first hierarchy in the hierarchical architecture of the network 10. The Ethernet frames communicated between the host devices 12A, 12B and the network devices 16A, 16B can include VLAN tags in accordance with IEEE-802.1q standard. Examples of suitable Ethernet frames for communication between the host device 12A and the network device 16A and the communication between the host device 12B and the network device 16B are illustrated in FIG. 2.

Host devices 12A, 12B, are coupled to network devices 16A, 16B using a point to point switched connection, for example, 10/100 fiber Ethernet (10/100FX). Nevertheless, those skilled in the art will recognize that other suitable mediums are available for providing a connectionless connection between the host devices 12A, 12B and the network devices 16A, 16B. The network devices 16A, 16B are coupled to network device 19 in a manner that uses point to point switched Ethernet or Ethernet over SONET/SDH (X.86) or any other suitable mechanism that supports the transmission and receipt of Ethernet frames. Communications between network device 16A, network device 19, and network device 16B identify a second network domain 20. The second network domain 20 represents a second network hierarchy in the network architecture of network 10. The format of the frames that are transferred between network device 16A, network device 19, and network device 16B is referred to as Ethernet encapsulated within Ethernet or MAC-in-MAC and are illustrated in FIG. 2 as frame format 48. Nevertheless, those skilled in the art will recognize that the frame format 48 illustrated in FIG. 2 includes optional fields.

Host device 12A and host device 12B operate as source and destination points in the network 10. Host devices 12A and 12B operate to connect a user to the network 10 and can, for example, connect a single workstation, laptop, personal computer, or other like electronic device to the network 10 or connect another network to the network 10. In one illustrative embodiment of the present invention, host device 12A and host device 12B are owned or operated by a user of the network 10 while network devices 16A, 16B, along with network device 19 are owned or operated by the network provider or service provider. Nevertheless, those skilled in the art will recognize that the network operator or provider can own or operate host devices 12A, 12B, network devices 16A, 16B, and network device 19.

Figure 7:
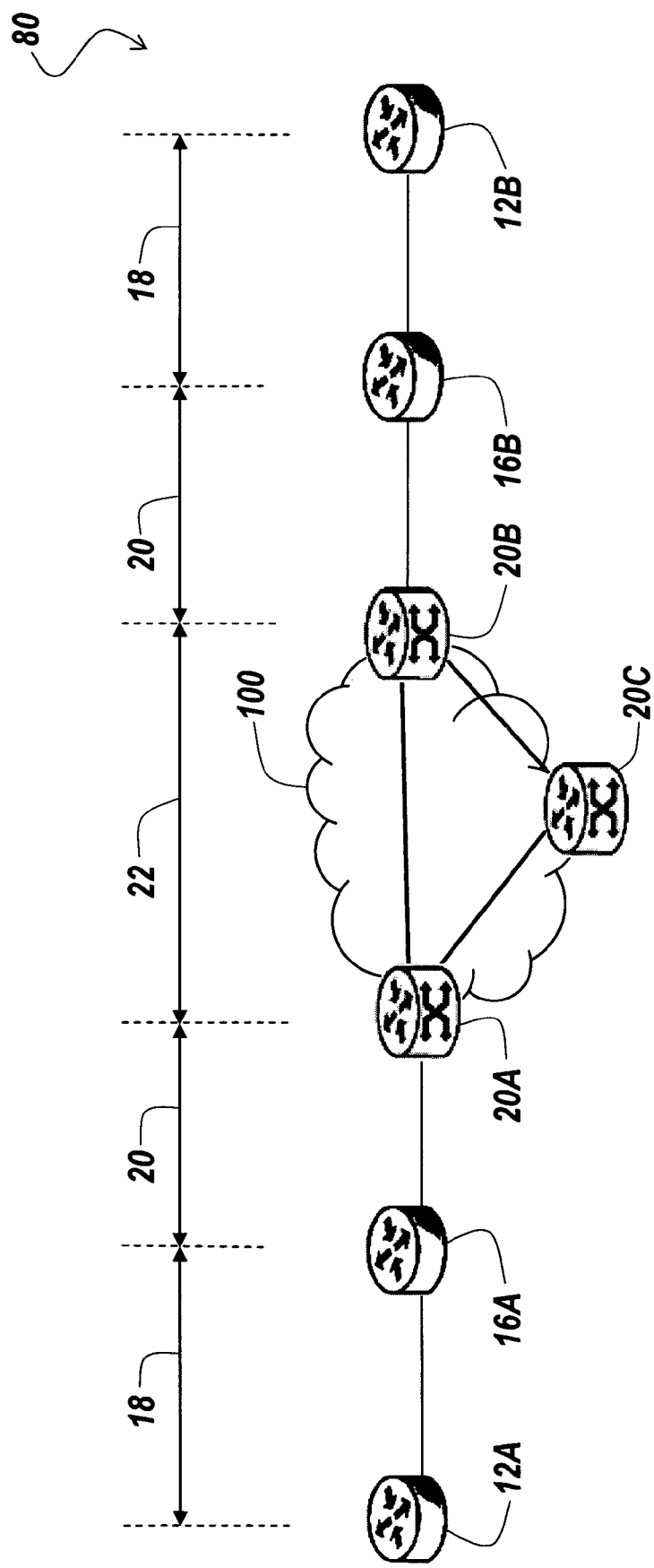
FIG. 7 illustrates a further exemplary network environment suitable for practicing the illustrative embodiment of the present invention.
Figure 8:
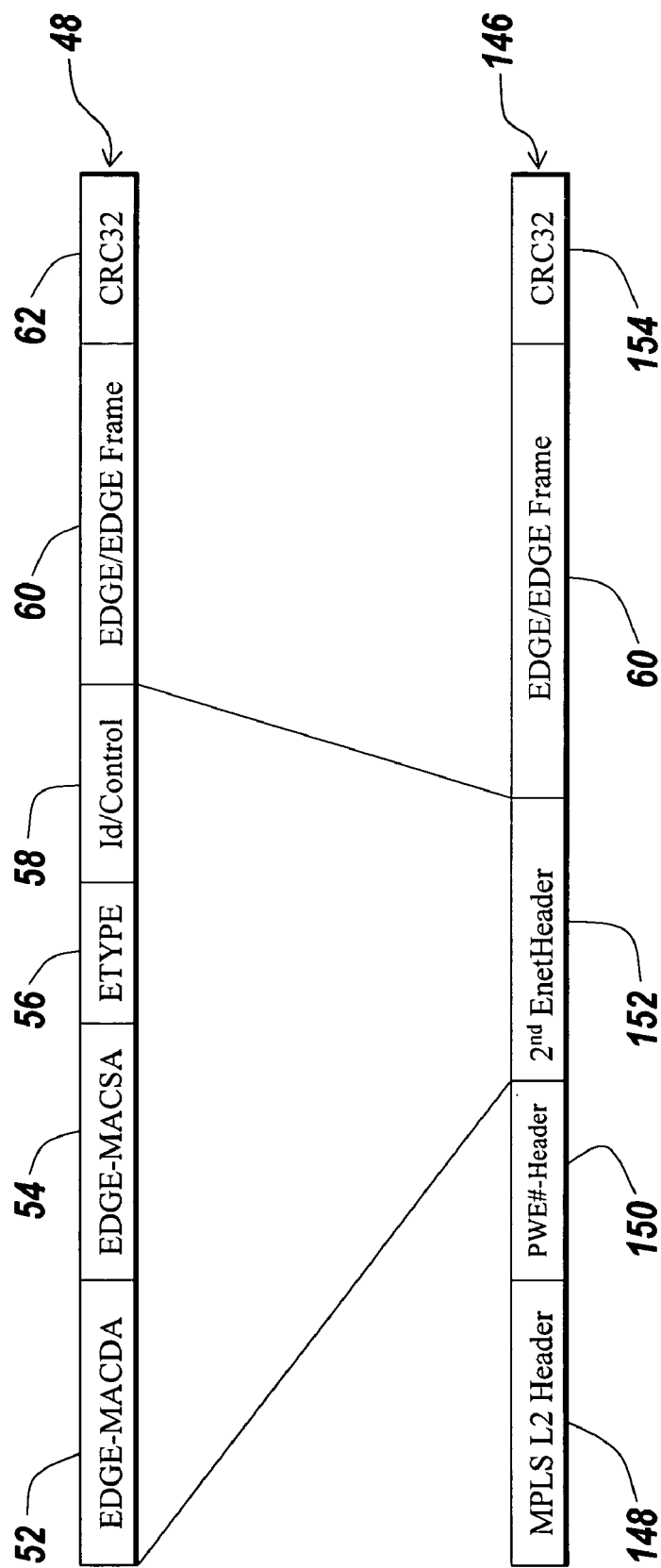
FIG. 8 illustrates an exemplary frame format suitable for use in the exemplary network environment illustrated in FIG. 7.
Figure 9:
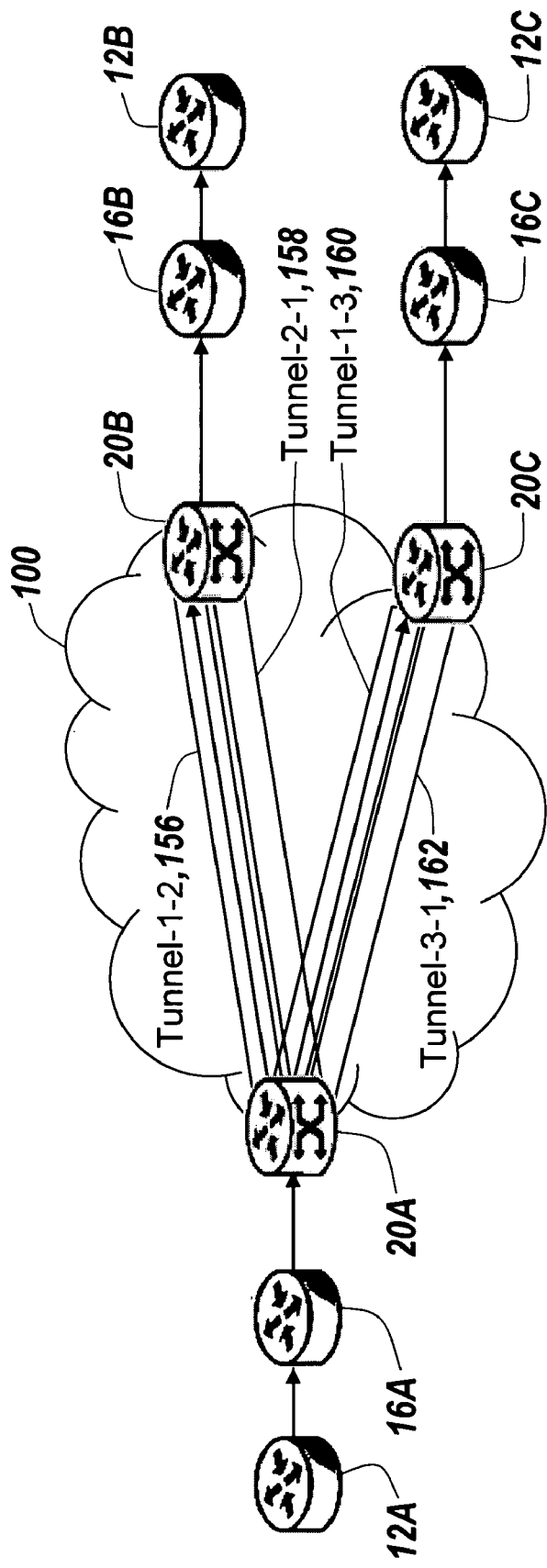
FIG. 9 illustrates a further exemplary network environment suitable for practicing the illustrative embodiment of the present invention.

Host devices 12A, 12B can include a number of ports interfacing with other electronic devices of a network user and one or more ports interfacing with network devices 16A, 16B. It is desirable to have each host device 12A and 12B include two or more ports interfacing with network devices 16A. 16B for purposes of redundancy, additional bandwidth, or both. The host device 12A and the host device 12B can connect to multiple network devices, however, each network device, for example, network device 16A ensures that only one such link between a network device and a host device is active at one time with the other links in a standby mode. Those skilled in the art will recognize that typically there are a number of host devices that connect to a single network device. Moreover, each network device, for example, network devices 16A and 16B can connect to multiple other network devices, such as multiple core devices or multiple core edge devices as illustrated in FIGS. 7-9 below. If a network device 16 connects to more than one other network device, network device 16 includes one or more control mechanisms, for example processing means 204 to ensure that one connection is active at a time between the two network devices and all other connections are in a standby mode. Nevertheless those skilled in the art will recognize that a single connection to a host device or a network device can include a group of links that are viewed as one, for example a connection configured in accordance with standard IEEE 802.3ad.

In operation, each host device 12A, 12B, and each network device 16A, 16B, and network device 19 are assigned a single MAC address. To facilitate discussion of the illustrative embodiment of the present invention network device 19 is assigned a single MAC address, nevertheless, those skilled in the art will recognize that practice of the illustrative embodiment of the present invention does not require network device 19 to have a MAC address assigned. When a host device has two or more links to a network device the host device uses the same MAC address when communicating on both links. In similar fashion, if a network device has two or more links to another network device, the network device uses the same MAC address when communicating on both links. This allows redundancy to be implemented in a manner that does not require remote ends, host device 12A and host device 12B, to know about a failure in the network 10.

Network devices 16A, 16B support a MAC address table organized and configured using a VPN identifier to define a transport path in the network 10. As such, each network device 16A, 16B learns the other MAC addresses of the other network devices in the network 10 and maps those MAC addresses to the source and destination devices associated with the identified VPN. Furthermore, network devices 16A, 16B support a number of Ethernet services such as frame replication of broadcast and multi-cast address frames. Discussion of VPN support and frame replication of broadcast and multi-cast address frames are discussed below in more detail. In this manner the number of MAC addresses that need to be managed by a core edge device, or a core device is significantly reduced. Accordingly, network 10 is readily scalable to increase or decrease in size because the addition of another network device 16 to the network increases the size or number of entries in the MAC address table of network device 19 by one. Hence, the MAC address table in network device 19 is readily maintained due to the small size allowing a network operator to realize a cost effective and scalable network architecture.

Each network device 16A, 16B, maintains a MAC address table, for example in storage means 216, which is maintainable per defined VPN's in the network 10. As such, when network device 16A receives a frame in a first frame format, network device 16A formats the frame into a frame in a second frame format by placing the MAC address of network device 16A in field 54 of the hierarchical MAC header and learns the addresses of a destination network device, for example network device 16B by mapping the MAC address of the destination host device within the defined VPN. Accordingly, network devices 16A, 16B can include and support a forwarding database or forwarding table, for example in storage means 216, that is keyed using the MAC address specifying the destination host device and a VPN identifier. The data for each keyed entry that belongs to a source or destination host device connected interface contains the identity of the source or destination host device interface. The data for each keyed entry that belongs to a network device interface contains the MAC address specifying a destination network device. In this manner, network device 16A uses the configured VPN identifier for the interface and performs a lookup of the MAC address of the destination host device within the VPN forwarding table for the received frame.

In operation of the network 10, communications between the host devices 12A, 12B and network devices 16A, 16B are carried out using frames in frame formats 24 and 36. Communications between network devices 16A, 16B, and network device 19 are carried out with frames in frame format 48, with or without all fields illustrated. Network devices 16A and 16B carry out the operations described above to format a received frame in a first frame format into a frame in a second frame format and to format a received frame from the second frame format to a frame in the first frame format.

For example, frames received by the network devices 16A and 16B from host device 12A or host device 12B are formatted into a hierarchical MAC frame format having tiered MAC addresses, such as an Ethernet frame encapsulated by another Ethernet frame. The hierarchical MAC frame includes sufficient information that allows other network devices, core devices and core edge devices to learn the source host device of each frame. Each hierarchical MAC frame can also include information that limits the replication of the broadcast and multi-cast frames within a VPN established in the network 10. The frame headers added to frames by the network devices 16A and 16B allow the network 10 to establish a hierarchy of LANS that are transparent to the host devices for the hierarchical MAC frame headers added by the network devices are stripped off by the network devices before a frame reaches a destination host device such as host device 12A or host device 12B. In this manner, network device 16 provides a cost effective scalable solution that minimizes the number of MAC address network device 19 must learn and maintain and, hence, allows a network operator or provider to increase or decrease the number of nodes in the network without increasing the complexity of the network control plane.

As discussed above, each network device 16A and network device 16B are assigned a single MAC address. The MAC address of each network device is used to identify the network device within the network 10. Optionally, a VPN identifier is included in the hierarchical MAC frame by the network device and is used by the network device and possibly a core edge device to identify and direct appropriate frames to and over a link configured as a VPN. Additionally, the VPN identifier is used to determine frame handling characteristics, such as broadcast scope that is particular to the identified VPN. The hierarchical MAC frame format 48 defines a new Ethernet type to support a VPN defined in the data link layer of a network. Field 56 holds a value that identifies the Ethernet type of a frame in frame format 48. The field 58 holds VPN ID and VPN control words. Field 58 is a 32 bit field as illustrated in FIG. 2. A more detailed discussion of field 58 and a VPN in the data link layer is discussed below in relation to FIG. 9.

Figure 6:
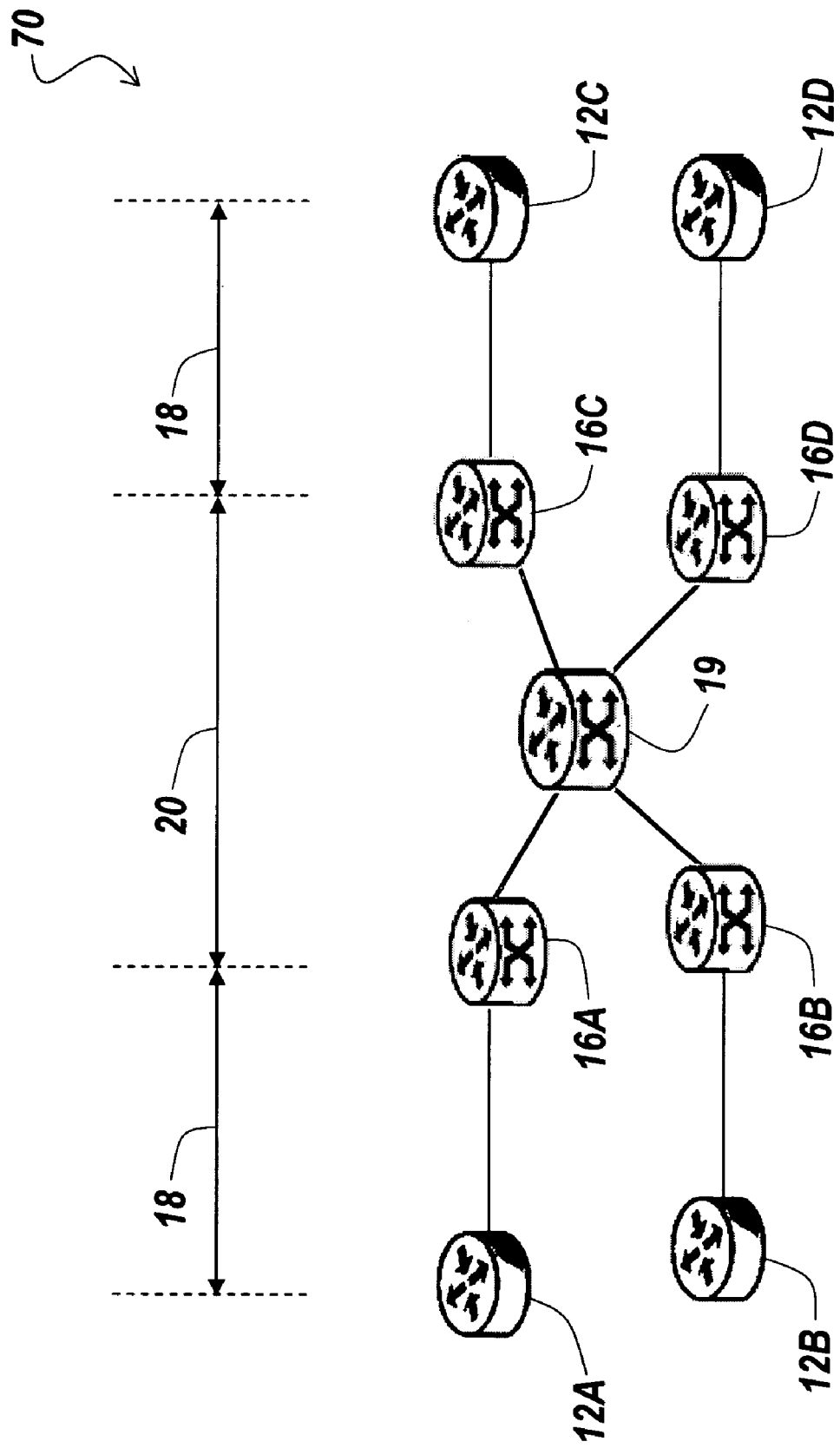
FIG. 6 illustrates another exemplary network environment suitable for practicing the illustrative embodiment of the present invention.

FIG. 6 illustrates another exemplary network architecture suitable for practicing the present invention. Network 70 includes host devices 12A-12D, network devices 16A-16D, and network device 19. Network 70 illustrates the scalability of an exemplary network architecture in accordance with the illustrative embodiment of the present invention. Network 70 illustrates the ability to scale by adding host devices and network devices to a network architecture without significantly increasing a network's operational complexity and cost. For example, network device 19 needs to know four MAC addresses in the network 70, that is, the MAC addresses of network devices 16A-16D. In this manner, a MAC address table of network device 19 is kept to a minimal size.

Host devices 12A-12D communicates with network devices 16A-16D in a frame format such as frame format 24 or frame format 36. Communications between host devices 12A-12D and network devices 16A-16D define a first network domain 18 or first network hierarchy. Communications between network devices 16A-16D define a second network domain 20 or second network hierarchy.

Network devices 16A-16D communicate with each other through network device 19 using frames in frame format 48. Network device 19 is considered a layer two network device that is able to understand and communicate with another network device in a data link layer protocol, for example a bridge or a switch. In operation network device 19 routes frames from the network devices 16A-16D using the hierarchical MAC addresses added to the frames received by each network device 16A-16D. The network device 19 is configurable to operate in a number of modes, for example, as a transparent bridge operating in promiscuous mode accepting every frame transmitted from each of the network devices 16A-16D or as a spawning tree bridge.

FIG. 7 illustrates a further exemplary network architecture suitable for practicing the present invention. Network 80 includes host devices 12A and 12B, network devices 16A and 16B and core edge devices 20A-20C. Network 80 includes a network backbone or network core 100. The backbone 100 supports point to point communication and multi-point communication allowing the core edge devices 20A-20C to perform point to point frame processing or multi-point frame processing. Backbone 100 is configurable as a MPLS backbone that integrates data link layer information about network links, for example, bandwidth, utilization and latency, into the network layer within a particular autonomous system or internet service provider in order to simplify and improve IP packet exchange. Nevertheless, the backbone 100 is configurable to support various bridging techniques and other protocols including, layer two tunneling protocol (L2TP), GRE tunneling protocol, IP in IP, and other suitable protocols An MPLS configured backbone provides network operators with an increased amount of flexibility to divert and route traffic around link failures, congestion, and bottlenecks. As such, core edge devices 20A-20C are configurable to operate as label edge routers (LER) that associate the frames received from network devices 16A and 16B with labels to form a frame in frame format 146 illustrated in FIG. 8. Those skilled in the art will appreciate that the labels provided by core edge devices 20A-20C contain information based on a routing table entry (i.e., destination, bandwidth, delay and other metrics, and other information such as differentiated service). In operation, network devices 16A and 16B communicate with core edge devices 20A-20C using frames in a frame format 48, with or without the optional fields. Communications between core edge devices 20A-20C identify a third network domain 22 or a third network hierarchy.

Core edge devices 20A-20C support and provide a number of frame processing techniques and methods depending on which interface the frame is received and the type of frame received. For example, frames received from other core edge devices over the backbone 100 are forwarded to network devices, such as network devices 16A and 16B. Another example based on an MPLS configured backbone 100 is frames received from network devices 16A and 16B are formatted to include an MPLS label and forwarded through the backbone 100 to another core edge device associated with the value in the MPLS label. Further, the backbone 100 is capable of supporting the ability to link a tunnel from, for example, core edge device 20A to core edge device 20B for transmission of data in one direction and to link a second tunnel in the reverse direction between the two same endpoints or core edge devices so that learning in one direction can be used to forward data in the reverse direction. An exemplary illustration of the core network configured with such tunnels is illustrated in FIG. 9 and is discussed below in more detail.

Each core edge device 20A-20C provides replication services. That is, network devices 16A and 16B are used to determine the destinations to which broadcast frames are replicated. Core edge devices 20A-20C receiving broadcast frames on an interface to the backbone 100 do not forward such frames to other core edge devices. They forward them to an interface associated with network devices 16A and 16B.

Core edge devices 20A-20C each maintains a forwarding database that can support two types of keys. The first key is used for frames received from backbone interfaces and depends on the architecture of the backbone network. Data associated with the first key often includes information that results in the receiving core edge device performing an additional lookup based on the second key. The second key is made up of a network device destination address and other information if the frame is associated with or includes a VPN identifier. Nevertheless, those skilled in the art will recognize that frame processing based on the first key is architecture dependent and as such, may not be performed by a core edge device 20A-20C.

Figure 7A:
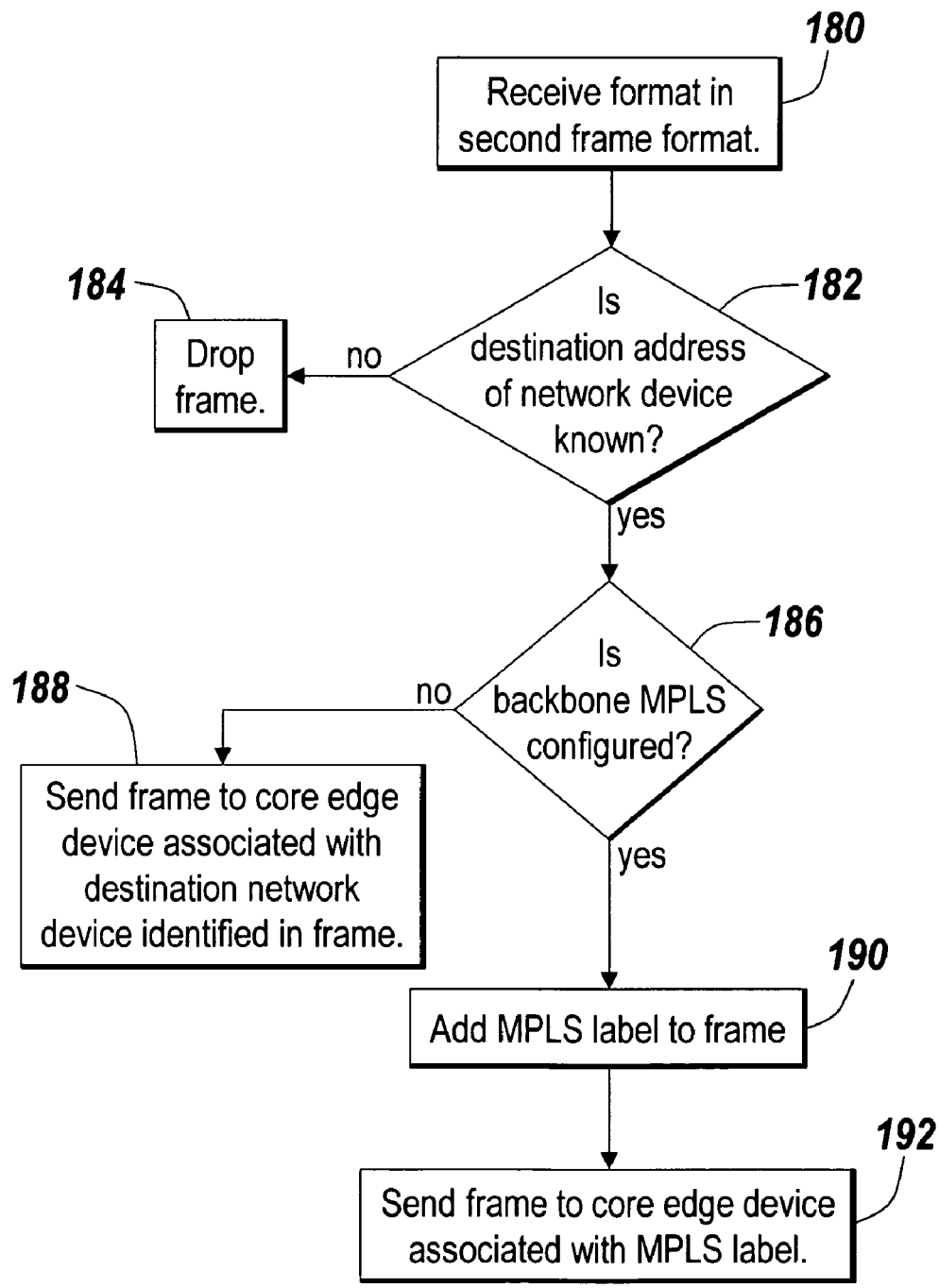
FIG. 7A is an exemplary flow diagram illustrating steps taken with the network illustrated in FIG. 7 to process frames.

FIG. 7A illustrates steps taken by core edge devices 20A-20C to process frames received from the network devices 16A and 16B. Core edge device 20A-20C process received frames in at least two different ways depending on the network device MAC destination address in the frame received from the network device. For example, in step 180, one of the core edge devices 20A-20C receives a frame in frame format 48. In step 182, the receiving core edge device determines if the destination address specifying the destination network device is known. If the MAC destination address in field 52 of a frame in frame format 48 is a unicast MAC destination address then such an address is considered a known MAC destination address. If the MAC destination address in field 52 is unknown core edge devices 20A-20C drops the frame (step 184). In step 186, the receiving core edge device determines how to forward the received frame. Frames received by core edge devices 20A-20C on an interface associated with network devices 16A and 16B that include a known MAC destination address in field 52 are forwarded based on a lookup result. In step 188, if the destination address specifying a network device is known and the backbone 100 is not MPLS configured, the frame is forwarded to a backbone interface of another core edge device. In step 190, if the backbone 100 is MPLS configured, or configured for a tunneling protocol, the frame is encapsulated with a MPLS label or tunnel identifier, if required, depending on the architecture backbone network. In step 192, the core edge device forwards the frame to another core edge device associated with the MPLS label or tunnel identifier. Moreover, if the frame received by the core edge device includes a destination address specifying a network device that is interfaced directly with the receiving core edge device the frame is forwarded to the interface of the core edge device associated with the specified network device and no additional encapsulation is performed by the core edge devices 20A-20C.

If the network devices 16A, 16B transmit a frame including a broadcast MAC, for example FF-FF-FF-FF-FF-FF in field 52 of a frame in frame format 48, the core edge devices 20A-20C that receive such a frame replicate the received frame to all other core edge devices. If the received frame with the broadcast MAC address in field 52 includes information in field 58 that identifies a VPN, the receiving core edge devices 20A-20C replicate the frame to the core edge devices that support connectivity for the VPN identified in field 58. Those skilled in the art will appreciate that core edge devices 20A-20C that receive frames that include a broadcast MAC address on an interface associated with backbone 100 are configurable to drop such frames and not forward such frames to other interfaces associated with the backbone 100.

FIG. 8 illustrates an exemplary frame format for use with a MPLS configured backbone network in accordance with the illustrative embodiment of the present invention. The illustrative embodiment of the present invention is able to transfer frames on a MPLS configured backbone network using an MPLS tunnel, as illustrated in FIG. 9. Those skilled in the art will recognize that an MPLS tunnel consists of a pair of unidirectional channel label switch paths. Frame format 146 illustrates a suitable format for use with an MPLS tunnel configured backbone core. Frame format 146 includes a field 148 to hold an MPLS header. Those skilled in the art will recognize that the format of the MPLS header in the field 148 is specific to the protocol used in the uplink to the core backbone 100. Field 150 is an optional field that is included in the frame format 146 for a MPLS configured backbone that includes an MPLS tunnel. Field 150 holds a value specifying a tunnel label for an MPLS tunnel. Nevertheless, those skilled in the art will recognize that the backbone is configurable for use with other tunneling technologies and protocols for example, IETF standard PWE3-CTRL.

Field 152 in frame format 146 includes field 52, 54, 56 and 58 of a frame in frame format 48. Field 60 holds the original frame from the host device to the network device. Field 154 holds a value for indicating a frame transmission error such as a CRC or checksum. Those skilled in the art will recognize that field 154 can be considered optional. The value held in field 154 is a newly calculated value based on the frame in frame format 146. Moreover, those skilled in the art will appreciate that if the core backbone 100 is configured for using MPLS for a tunneling protocol, the QOS bits in field 58 of a frame in format 48 are mapped to and from EXP bits in the E-LSP tunnels.

FIG. 9 illustrates an exemplary network architecture in which the core backbone 100 is configured for MPLS tunneling. The core backbone 100 includes a tunnel 156 and a tunnel 158 established between core edge device 20A and core edge device 20B. Tunnel 156 passes frames from the core edge device 20A to the core edge device 20B. Tunnel 158 passes frames from the core edge device 20B to the core edge device 20A. The core backbone 100 further includes a tunnel 160 and a tunnel 162 between the core edge device 20A and the core edge device 20C. Tunnel 160 passes frames from core edge device 20A to core edge device 20C. Tunnel 162 passes frames from core edge device 20C to core edge device 20A. Those skilled in the art will recognize that the backbone core 100 can contain other tunnels, for example, between core edge device 20B and 20C or between other core edge devices associated with the core backbone 100, but not illustrated.

Figure 10:
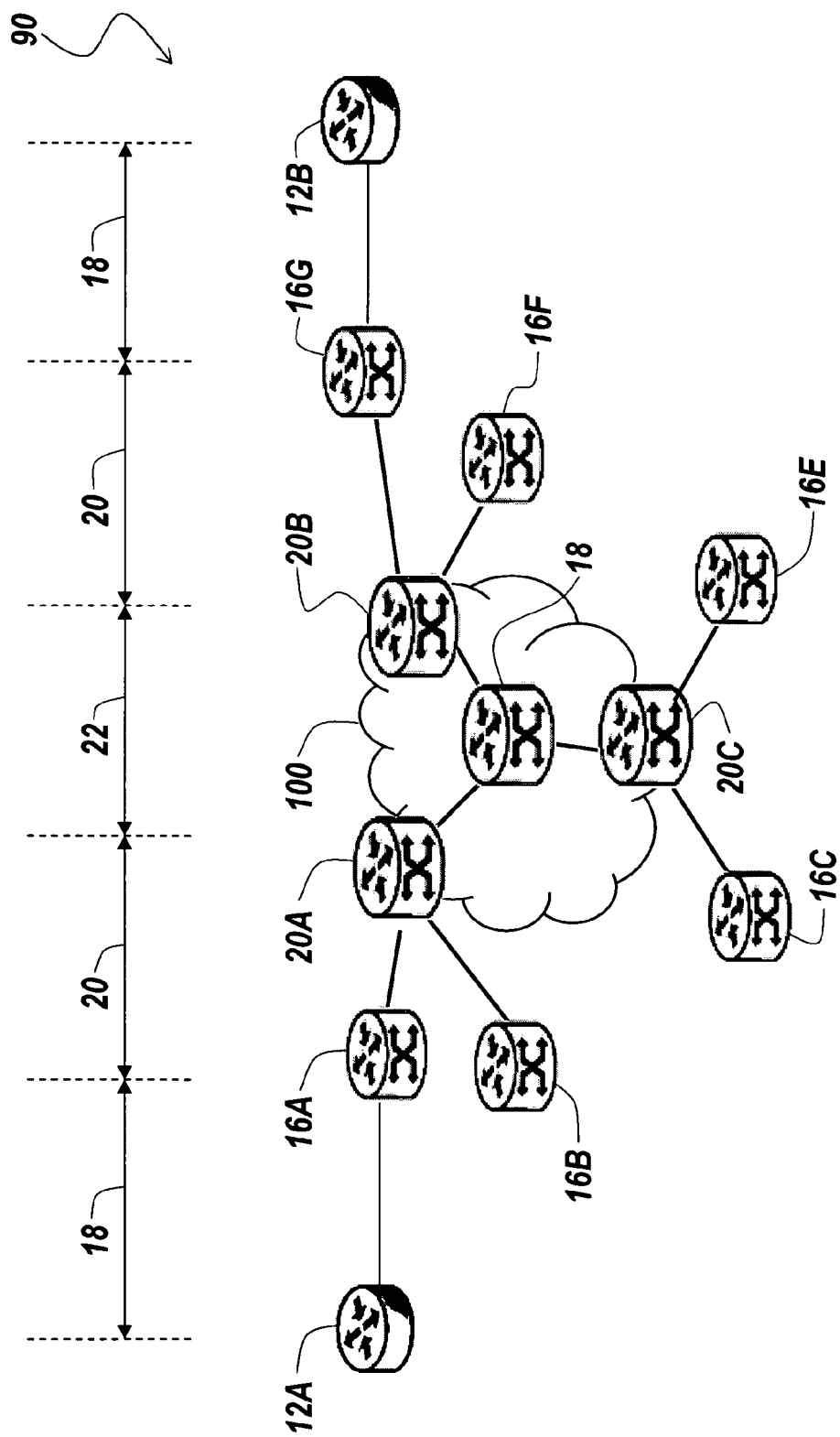
FIG. 10 illustrates an additional exemplary network environment suitable for practicing the illustrative embodiment of the present invention.

FIG. 10 illustrates an additional exemplary network architecture suitable for practicing the illustrative embodiment of the present invention. Network 90 includes host devices 12A, 12B, network devices 16A-16G, core edge devices 20A-20C, and core device 18. Core device 18 is configurable as bridge, switch or router to traffic information within the network backbone 100 to the appropriate core edge device 20A-20C using a frame in format with an MPLS label such as frame format 146 or other suitable frame format.

While the present invention has been described with reference to an illustrative embodiment thereof, one skilled in the art will appreciate that there are changes in form and detail that may be made without departing from the intended scope of the present invention that is defined in the pending claims. For example, the illustrative embodiment of the present invention uses a single MAC address per communication device in the network. Nevertheless, the illustrative embodiment of the present invention is configurable to assign and use a MAC address per interface of each network device. In addition, the illustrative embodiment of the present invention is adaptable to use dynamic MAC addressing so that MAC addresses are assigned dynamically either to a network device or to an interface of a network device. Moreover, the MAC address can utilize a big-endian format or a little-endian format. Furthermore, it is possible to place the second tier MAC addresses in fields other than the first two fields in a frame.

Nevertheless, those skilled in the art will recognize that the illustrative invention is suitable for use with a core network configured to use pseudo wires as defined in Internet Engineering Task Force (IETF) standard PWE3-ENET. Accordingly, those skilled in the art will recognize pseudo-wires are paths that are carried in a tunnel and therefore have two labels. One label is an outer label (i.e. the tunnel label) and the second label is an inner label defining what to do with the frame when it reaches the end of the tunnel. However, apparatuses, methods, and network architectures in accordance with the illustrative embodiment of the present invention eliminate the need of the second or inner label because the outer MAC header of a frame in frame format 48 defines for the device at the end of the tunnel what to do with the frame, and hence, practice of the illustrative embodiment of the present invention in a network configured with pseudo-wires places a known constant value in the field of the inner label.

What is claimed is:

1. A packet-forwarding apparatus for use in a network comprising network devices, the apparatus comprising,
a storage for storing an address table having a number of entries comprising data link layer addresses for the network devices;
an input to receive a first frame in a first frame format, the first frame format comprising a first data link layer header,
wherein the first frame format represents a first tier of data link layer addresses in the network such that the network has a hierarchy achieved through tiered data link layer addressing;
a framing mechanism to encapsulate the first frame with a second data link layer header to form a second frame format, the second frame format representing a second tier of data link layer addresses in the network hierarchy;
an output to forward the frame in the second frame format toward a destination electronic device; and
a processor for updating the address table, wherein the number of entries in the address table increases linearly for each network device with a data link layer address that is associated with the second tier of the network hierarchy added to the network.

2. The apparatus of claim 1, wherein the framing mechanism adds a trailer to the first frame to form the second frame.

3. The apparatus of claim 1, wherein the apparatus is a switch.

4. The apparatus of claim 1, wherein the output forwards the frame in the second frame format based on a destination address from the first frame format.

5. The apparatus of claim 1, wherein the framing mechanism encapsulates the first frame independent of the location of the apparatus in the network hierarchy.

6. A device readable medium holding device readable instructions for performing a method in an electronic device for use in a network comprising network devices, the electronic device storing an address table having a number of entries comprising data link layer addresses for the network devices, the method comprising the steps of,
parsing a portion of a first frame in a first frame format received on an input of the electronic device to identify a destination address of the frame, the first frame format having a first data link layer source address and a first data link layer destination address, wherein the first frame format represents a first tier of data link layer addresses in the network such that the network has a hierarchy achieved through tiered data link layer addressing;
formatting the frame in the first frame format into a second frame format in the electronic device, wherein the second frame format represents a second tier of data link layer addresses in the network hierarchy, the second frame format having a second data link layer source address and a second data link layer destination address;
forwarding the frame in the second frame format toward a destination electronic device; and
updating the address table, wherein the number of entries in the address table increases linearly for each network device with a data link layer address that is associated with the second tier of the network hierarchy added to the network.

7. The medium of claim 6, wherein the step of formatting comprises the step of appending a trailer to the frame in the first frame format.

8. The medium of claim 6, wherein the step of formatting comprises the step of encapsulating the frame in the first frame format to format the frame into the second frame format.

9. The medium of claim 6, wherein the first frame format includes a first MAC source address and a first MAC destination address.

10. The medium of claim 6, wherein the second frame format includes a second MAC source address and a second MAC destination address.

11. The medium of claim 6 further comprising the step of, adding a label to the frame in the second frame format.

12. The medium of claim 6 further comprising the steps of,
receiving one or more of the frames in the second frame format from another electronic device associated with the network; and
decapsulating one of the received frames in the second frame format to return the received frame to the first frame format.

13. The medium of claim 12 further comprising the step of, forwarding the first frame in the first format to the destination address identified in the destination address field of the frame in the first frame format.

14. The medium of claim 6, wherein the step of forwarding the frame in the second frame format is performed based on a destination address from the first frame format.

15. The medium of claim 6, wherein the step of formatting the frame in the first frame format into a second frame format is performed independent of the location of the electronic device in the network hierarchy.

16. A method performed in an electronic device for use in a network comprising network devices, the electronic device storing an address table having a number of entries comprising data link layer addresses for the network devices, the method comprising the steps of,
parsing a portion of a first frame in a first frame format received on an input of the electronic device to identify a destination address of the frame, the first frame format having a first data link layer source address and a first data link layer destination address, wherein the first frame format represents a first tier of data link layer addresses in the network such that the network has a hierarchy achieved through tiered data link layer addressing;
formatting the frame in the first frame format into a second frame format in the electronic device, wherein the second frame format represents a second tier of data link layer addresses in the network hierarchy, the second frame format having a second data link layer source address and a second data link layer destination address;
forwarding the frame in the second frame format toward a destination electronic device; and
updating the address table, wherein the number of entries in the address table increases linearly for each network device with a data link layer address that is associated with the second tier of the network hierarchy added to the network.

17. The method of claim 16, wherein the step of formatting comprises the step of appending a trailer to the frame in the first frame format.

18. The method of claim 16, wherein the step of formatting comprises the step of encapsulating the frame in the first frame format to format the frame into the second frame format.

19. The method of claim 16, wherein the first frame format includes a first MAC source address and a first MAC destination address.

20. The method of claim 16, wherein the second frame format includes a second MAC source address and a second MAC destination address.

21. The method of claim 16 further comprising the step of, adding a label to the frame in the second format.

22. The method of claim 16 further comprising the steps of,
receiving one or more of the frames in the second frame format from another electronic device associated with the network; and
decapsulating one of the received frames in the second frame format to return the received frame to the first frame format.

23. The method of claim 22 further comprising the step of, forwarding the frame in the first format to the destination address identified in the destination address field of the frame in the first frame format.

24. The method of claim 16, wherein he step of forwarding the frame in the second frame format is performed based on a destination address from the first frame format.

25. The method of claim 16, wherein the step of formatting the frame in the first frame format into a second frame format is performed independent of the location of the electronic device in the network hierarchy.

* * * * *